United States Patent [19]

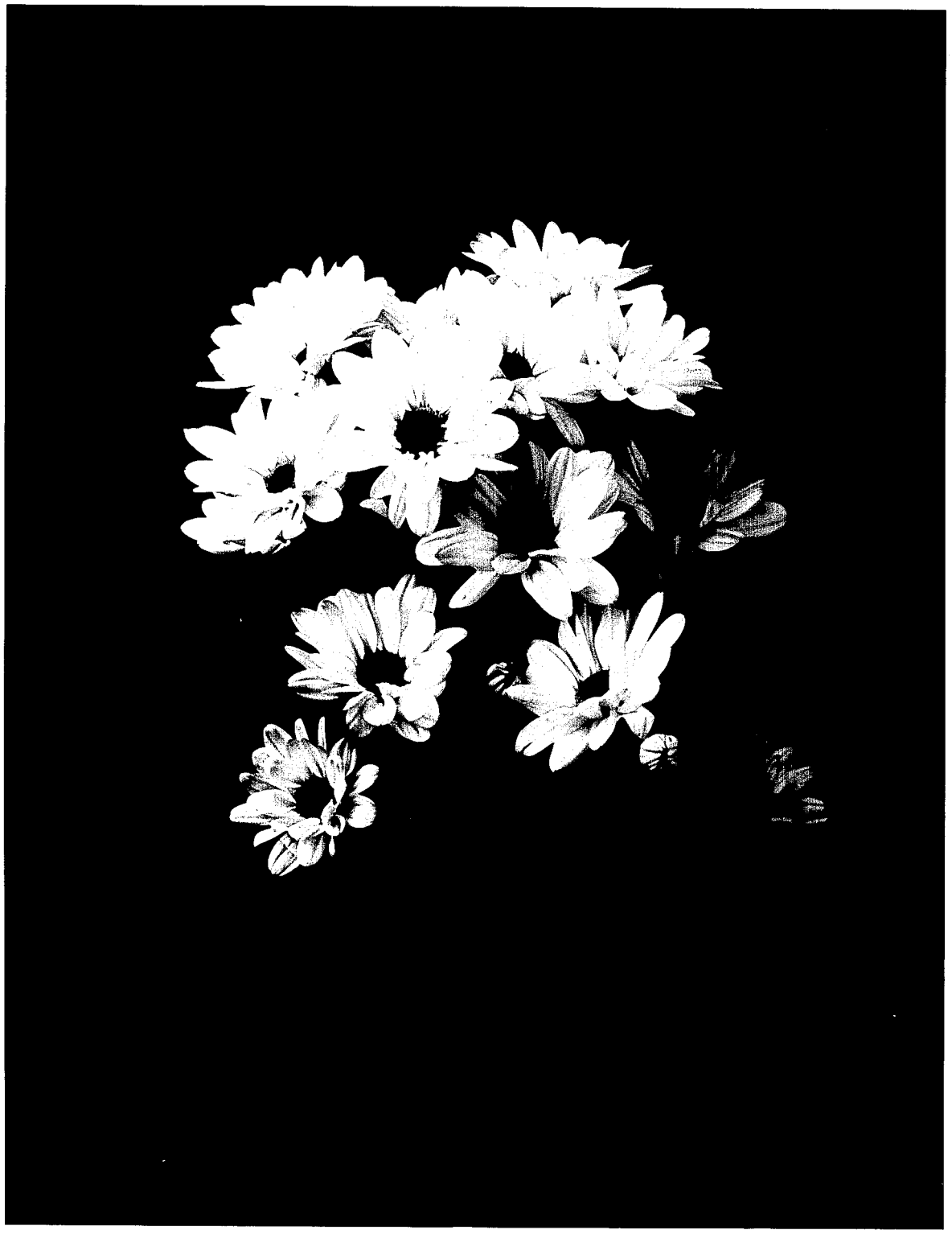

Van der Knapp

[11] Patent Number: Plant 6,737

[45] Date of Patent: Apr. 11, 1989

[54] CHRYSANTHEMUM PLANT NAMED BROADWAY

[75] Inventor: Jacques C. M. Van der Knapp, De Lier, Netherlands

[73] Assignee: Fides Beheer B.V., De Lier, Netherlands

[21] Appl. No.: 123,904

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum cultivar named Broadway, having generally flat capitulum form and single capitulum type, light pink ray floret color, and a dark anthocyanin dot in the center of the disc florets.

1 Drawing Sheet

The present invention comprises a new and distinct cultivar of *Chrysanthemum morifolium,* hereinafter referred to by the cultivar name Broadway.

Broadway is a product of a planned breeding program which had the objective of creating new Chrysanthemum cultivars with single capitulum type, pink ray floret color, an anthocyanin dot in the flower center, nine week response, and the ability to produce commercially acceptable quality in year-round cut mum program. Such traits in combination were not present or needed improvement in previously available commercial cultivars.

Broadway was originated from a hybridization made by applicant in a controlled breeding program in De Lier, Holland in 1984. The female parent was Glamour. The male parent of Broadway was BZN. Both parents are unpatented but commercially well known in Europe.

Broadway was discovered and selected as one flowering plant within the progeny of the stated parentage by Jacques C. M. Van der Knapp in September 1984 in a controlled environment in De Lier, Holland.

The first act of asexual reproduction of Broadway was accomplished when vegetative cuttings where taken from the initial selection in November 1984 in a controlled environment in De Lier, Holland by a technician working under formulations established and supervised by Jacques C. M. Van der Knapp. Horticultural examination of selected units initiated in April 1986 has demonstrated that the combination of characteristics as herein disclosed for Broadway are firmly fixed and are retained through successive generations of asexual reproduction.

Broadway has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Broadway, which in combination distinguish this Chrysanthemum as a new and distinct cultivar:

1. Generally flat capitulum form.
2. Single capitulum type.
3. Soft pink ray floret.

4. Dark pink dot in flower center.
5. No or very late pollen production.
6. Diameter across face of the capitulum is 65–75 mm.
7. Green (immature) to yellow (mature) disc florets.

Of the many commercial cultivars known to the present inventor, the most similar in comparison to Broadway is Glamour. In comparison to Glamour, Broadway has less vigor, a different pink ray floret color, and a dark spot in the center of the disc florets. The capitulum form and capitulum type are similar to those same characteristics of Glamour.

The accompanying photographic drawing shows in side elevation the typical inflorescence and foliage characteristics of Broadway, with color being as nearly true as possible with illustrations of this type.

In the following description, color references are made to The Royal Horticultural Society Colour Chart. The color values were determined between 11:00–12:00 a.m. in June 1986 under natural daylight at De Lier, Holland.

Classification:

*Botanical.*—*Chrysanthemum morifolium,* Ramat., cv. Broadway.

*Commercial.*—Cut daisy spray.

INFLORESCENCE

A. Capitulum:

*Form.*—When mature, flat to slightly cupped.

*Type.*—Single.

*Diameter across face.*—60–70 mm.

B. Corolla of ray florets:

*Color (general tonality from a distance of three meters).*—Pale pink.

*Color (upper surface).*—65D. (This color appears in the photograph but the ray florets in the photo appear to be more white than they actually are).

C. Corolla of disc florets:

*Color (mature).*—Yellow with dark pink center.

*Color (immature).*—Green with a more red brown center (approximately 177A).

D. Reproductive organs:

*Androecium.*—Present only in disc florets, numerous.

*Gynoecium.*—Present in both disc and ray florets, numerous.

PLANT

A. General appearance:
*Height.*—85 cm.
B. Foliage:
*Color* (*upper surface*).—147A.
*Color* (*under surface*).—147B.

*Shape.*—Pinnately lobed.

I claim:

1. A new and distinct cultivar of Chrysanthemum plant named Broadway, as illustrated and described, and parts thereof.

* * * * *